United States Patent [19]

Chowdhury et al.

[11] Patent Number: 5,363,845
[45] Date of Patent: Nov. 15, 1994

[54] BREAST COIL FOR MAGNETIC RESONANCE IMAGING

[75] Inventors: Sruba Chowdhury, Milwaukee; Eddy B. Boskamp, Menomonee Falls, both of Wis.

[73] Assignee: Medical Advances, Inc., Milwaukee, Wis.

[21] Appl. No.: 106,294

[22] Filed: Aug. 13, 1993

[51] Int. Cl.$^5$ ............................................ A61B 5/055
[52] U.S. Cl. .................... 128/653.5; 324/318; 324/322
[58] Field of Search .................... 128/653.2, 653.5; 324/318, 322

[56] References Cited

U.S. PATENT DOCUMENTS

| 4,534,358 | 8/1985 | Young | 128/653.2 |
| 4,924,184 | 5/1990 | Yoda | 324/318 |
| 5,139,024 | 8/1992 | Bryant et al. | 128/653.5 |

FOREIGN PATENT DOCUMENTS

| 0176353 | 4/1986 | European Pat. Off. | 128/653.2 |
| 04332531 | 11/1992 | Japan | 128/653.5 |

Primary Examiner—Ruth S. Smith
Attorney, Agent, or Firm—Quarles & Brady

[57] ABSTRACT

A local coil for magnetic resonance imaging of the breast employs two generally cylindrical coils isolated from each other by a radio frequency shield. The coils comprise multiple loops displaced along the axis of the cylinder and connected in parallel to provide uniform coverage of the volume. Coils may be activated individually or at the same time with their signals combined. In the former case, the non-activated coil is actively decoupled by stimulating its decoupling circuit network with a DC bias signal from the system. The activated coil decouples passively during transmit.

3 Claims, 4 Drawing Sheets

BREAST COIL FOR MAGNETIC RESONANCE IMAGING

BACKGROUND OF THE INVENTION

1. Field of the Invention

The field of the invention is magnetic resonance imaging (MRI) and, in particular, local coils for use in receiving and transmitting radio frequency signals in MRI equipment.

2. Background Art (a) Breast Imaging

Breast augmentation or reconstructive surgery may employ, implants containing silicone. The silicone used in breast prosthesis is composed of poly-dimethylsiloxane with varying degrees of polymerization. In one commercially available implant, the silicone is approximately 40% polymerized.

Rupture and leakage of the membrane containing the silicone is a known complication of these procedures. The prevalence of complications is not known because patients may be asymptomatic, however, in light of anecdotal reports of a possible link between silicone leakage and systemic autoimmure disease, it is important to develop a sensitive non-invasive method to detect leaks.

The leak or rupture may occur anywhere over the surface of an implant and therefore the use of three-dimensional medical imaging techniques is desirable. Such imaging would, in theory, allow careful scrutiny of the entire surface of the implant and the detection of even small pockets of migrating silicone near that surface.

(b) MRI Imaging

Nuclear magnetic resonance imaging ("MRI") is one technique capable of the necessary three-dimensional imaging. In MRI, a uniform magnetic field ($B_0$) is applied to an imaged object along the Z-axis of a Cartesian coordinate system, the origin of which is within the imaged object. The effect of the magnetic field $B_0$ is to align the object's nuclear spins along the Z-axis. In response to radio frequency (RF) pulses of the proper frequency, oriented within the XY plane, the nuclei resonate at their Larmor frequencies according to the following equations:

$$\omega = \gamma \beta_0 \tag{1}$$

where $\omega$ is the Larmor frequency, and 65 is the: gyromagnetic ratio which is a property of the particular nucleus. Water, because of its relative abundance in biological tissue and the properties of its proton nuclei, is of principle concern in most imaging.

In a typical imaging sequence of an axial slice, the RF signal, centered about the Larmor frequency of water, is applied to the imaged object at the same time a magnetic field gradient $G_z$ is applied. The gradient field $G_z$ causes only the nuclei in a slice with a limited width through the object along the XY plane, to have the resonant frequency and to be excited into resonance.

After the excitation of the nuclei in the slice, magnetic field gradients are applied along the X and Y axes. The gradient along the X axis, $G_x$, causes the nuclei to precess at different frequencies depending on their position along the X axis, that is, $G_x$ spatially encodes the precessing nuclei by frequency. The Y axis gradient, $G_y$, is increment through a series of values and encodes the Y position into the rate of change of the phase of the precessing nuclei as a function of gradient amplitude, a process typically referred to as phase encoding.

A weak nuclear magnetic resonance generated by the precessing nuclei may be sensed by the RF coil and recorded as an NMR signal. From this NMR signal, a slice image may be derived according to well known reconstruction techniques. An overview of NMR image reconstruction is contained in the book, *Magnetic Resonance Imaging, Principles and Applications,* by D. N. Kean and M. A. Smith.

The value of the gyromagnetic ratio $\gamma$ for protons in water is 4.26 kHz/Gauss and therefore in a 1.5 Tesla polarizing magnetic field $B_0$, the resonant or Larmor frequency of water protons is approximately 63.9 megahertz. The other primary constituent in biological tissue is fat. The Larmor frequency of protons in fat is approximately 203 hertz higher than that of the protons in water in a 1.5 Tesla polarizing field.

In that same field, the Larmor frequency of silicon protons is approximately 102 hertz higher than the protons of fat and 305 hertz higher than the protons of water. Accordingly, in theory, this difference between the Larmor frequencies of different isotopes may be exploited to distinguish these different materials in the three dimensional MRI image.

(c) Local Coils

The quality of the image produced by MRI techniques is dependent, in part, on the strength of the NMR signal received from the precessing nuclei. For this reason, it is optimal to use an independent RF receiving coil placed in close proximity to the region of interest of the imaged object in order to improve the strength of this received signal. Such coils are termed "local coils" or "surface coils". The smaller area of the local coil permits it to accurately focus on the NMR signal from the region of interest. Further, the RF energy of the field of such a local coil is concentrated in a smaller volume giving rise to improved signal-to-noise ratio in the acquired NMR signal.

SUMMARY OF THE INVENTION

The present invention provides a local coil suitable for imaging the two human breasts, either individually or at the same time, through the use of two resonating structures or coils with a cavity in which a breast can be suspended. Importantly, the coil structure is selected to provide an improved uniformity in the region of sensitivity and is shielded to reduce interaction between the coils and between the coils and the bore of the magnet to produce signals with high signal-to-noise ratios.

Specifically, a first and second coil form are used to define adjacent volumes disposed and sized for receiving, respectively, the first and second breasts through first open ends of the first and second coil forms. Attached to the forms, so as to receive a first and second RF signal from the volumes of the forms, are a first and second coil. A radio frequency shield is positioned between the first and second coil to limit the sensitivity of the first coil to an RF signal in the second volume and to limit the sensitivity of second coil to an RF signal in the first volume.

The RF shield may be a tubular conductor fitting around the first coil and having an open end corresponding to the open end of the first coil formed. A second tubular conductor is also fitted around the second coil. The shield conductor is wrapped around a tube of diameter much larger than coil tube diameter. The coil tube is almost concentric to the shield tube at most places.

It is one object of the invention to provide a breast coil with improved signal-to-noise ratio of the coils and that may be operated bi-laterally for imaging both breasts at once. Although intuitively one might expect overlap between the regions of sensitivities of adjacent breast coils to be advantageous, the present invention recognizes that such interaction in fact decreases the signal-to-noise ratio of the acquired, combined signal. This reduced signal-to-noise ratio is thought to be the result of a de-tuning of the coils by their interaction. Even partial shielding provided by the RF shield significantly reduces the interaction between the coils.

The first and second coil may comprise a plurality of parallel connected conductive loops arranged coaxially along an axis of symmetry of the respective breast.

It is another object of the invention to select a coil geometry that provides a uniform region of sensitivity about the volume of the breast. The modified solenoid structure with the multiple conductive loops produces a highly uniform region of sensitivity.

The first and second coils each have their own decoupling network. Each decoupling network detunes its coil when it receives a DC decoupling current from the MRI system DC in the transmit mode. A switch box may direct a decoupling DC signal to the opposite coil when either coil alone is being employed to receive the NMR signal. The switch box may also combine the signals from the two coils through a combiner network.

Thus, another object of the invention is to further decrease interaction between the coils by de-tuning the coil not in use in unilateral imaging.

The first and second coil form may be attached to the upper surface of a pallet, at their second ends, so that they extend upward from the pallet by a height. A removable cushion may be fitted against the coil forms, the cushion having a first portion fitting against the upper surface of the pallet and extending the height above the upper surface against the first side of the first and second coil to support the head and shoulder of the patient when the patient is positioned on the coil forms. A second portion of the cushion may fit against the upper surface of the pallet and extend the height above the upper surface against a second side of the first and second coil form to support the trunk of the patient when the patient is positioned on the coil forms. The first and second portions of the removable cushion are sized and arranged so that they may be interchanged to accommodate "head first" or "feet first" positioning of the patient on the table without removal of the pallet from the table.

It is thus another object of the invention to accommodate different imaging orientations without requiring repositioning of the coil forms with respect to the table.

Other objects and advantages besides those discussed above will be apparent to those skilled in the art from the description of the preferred embodiment of the invention which follows. Thus, in the description, reference is made to the accompanying drawings, which form part hereof, and which illustrate one example of the invention. Such example, however, is not exhaustive of the various alternative forms of the invention. Therefore, reference should be made to the claims which follow the description for determining the full scope of the invention.

DETAILED DESCRIPTION OF THE PREFERRED EMBODIMENT

Figure 1:
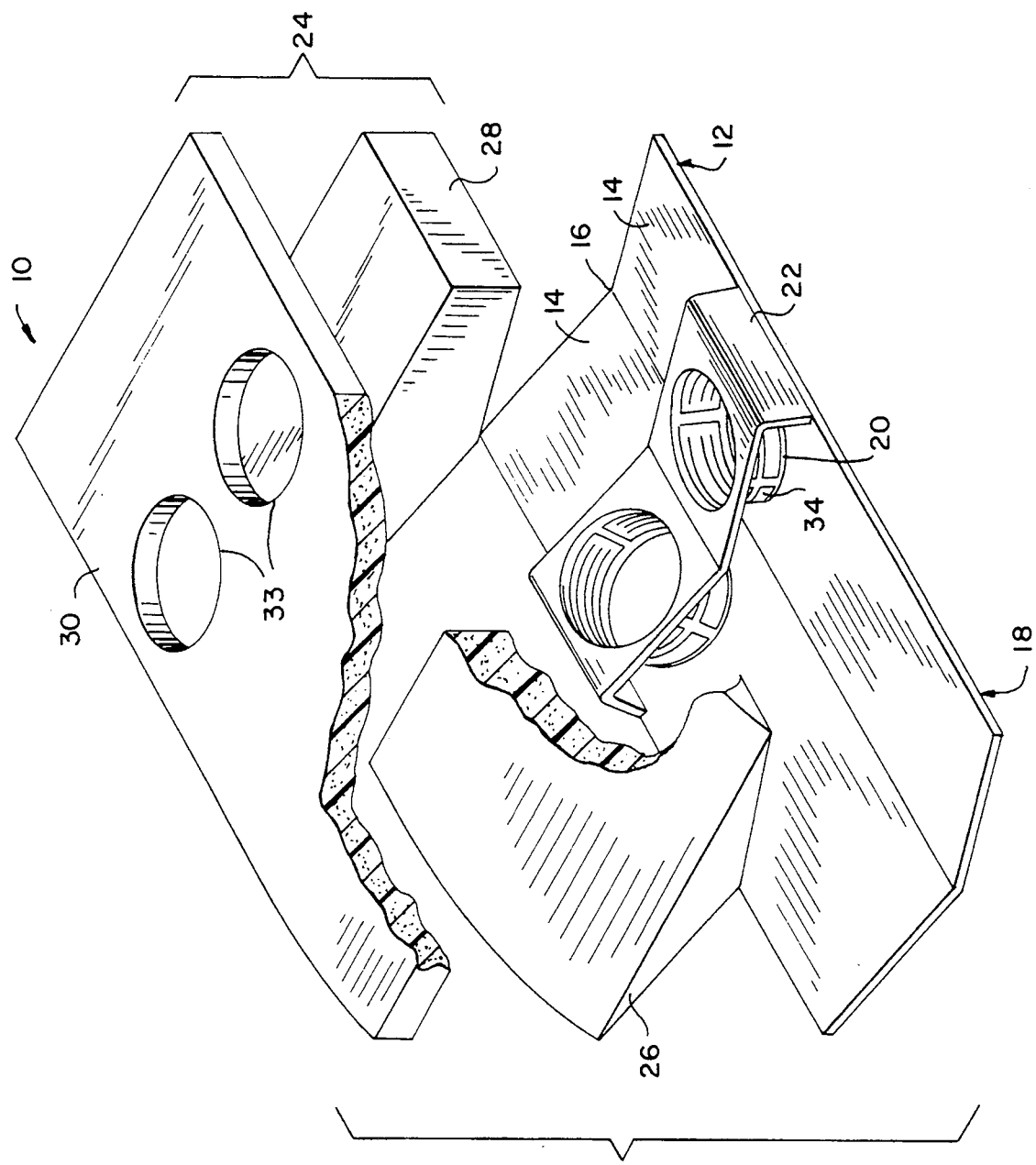
FIG. 1 is an exploded, perspective view, in partial cutaway, of the local coil of the present invention showing the coil forms as positioned within removable cushions to allow for "head first" or "feet first" positioning of the patient within the bore of an MRI magnet.

Referring to FIG. 1, the local coil 10 of the present invention includes a pallet 12 formed of two longitudinally extending planar sheets 14 joined at a midline 16 so that the pallet 12 has a shallow V-shaped cross-section in the transverse plane. The bottom plate is shaped such that it conforms to the patient tray of the MRI system and antislide strip 18 (not visible) on the lower surface of the bottom plate prevents the plate from sliding.

A first and second coil form 20, being each a cylindrical tube, are attached to the upper surface of the pallet 12 to extend upward therefrom. Each coil form 20 is attached at its base to the center of one of the sheets 14 of the pallet 12 so that the axes of the coil forms 20 intersect above the midline 16 and so that the coil forms are equally spaced from the longitudinal ends of the pallet 12. The upper ends of the coil forms 20, opposite their bases and thus not attached to the pallet 12, define an open volume each for receiving one human breast.

A cowling 22 fits across the upper ends of the coil forms 20 and has holes matching to the open ends of the coil forms 20. The cowling 22 generally provides an upper surface positioned above but parallel to the upper surface of the pallet 12 that may support a patient's sternum as will be described.

The pallet 12, the coil forms 20, and the cowling 22 are constructed out of a non-conductive plastic material to minimize interference between these structures and the electromagnetic fields to be detected.

Covering the pallet 12, the cowling 22 and the coil forms 20 is a removable foam cushion 24 which includes a trunk cushion 26 and a head cushion 28. The trunk cushion fits between one end of the pallet 12 and the cowling 22 against the upper surface of the pallet 12, conforming thereto, and rises by substantially the same height as the coil forms 20 so that its top surface, near the cowling 22, is flush with the top of cowling 22. The opposite end of the trunk cushion 26, removed from the cowling 22, tapers downward toward the upper surface of one longitudinal end of pallet 12 to provide a tapered ramp for supporting the pelvis and trunk of the patient up to cowling 22. The ramp head and top flat pad together form a unit pad which is upholstered for patient comfort.

The head cushion 28 fits on the opposite side of the cowling 22, against the other side of the cowling 22, and has a lower surface conforming to the upper surface of the pallet 12. The head cushion 28 provides an upper surface flush with the cowling 22, near the cowling 22, and extends to the opposite end of the pallet 12 without a tapering so as to provide a support for the patient's head and arms when the patient's sternum is positioned over the cowling 22 and the patient's breasts are received within the volumes of the coil forms 20.

A foam slab 30 is glued to the top of the head and trunk cushions 26 and 28 and has essentially uniform thickness through which holes 33 are cut corresponding to the openings of the coil forms 20. The foam slab 30 thus provides a single cushion surface conforming to the upper surface of cushion 26 of cowling 22 and of cushion 28 and serves to connect the head and trunk cushions 28 and 26 so they may be lifted and turned as a single piece.

The central positioning of the coil forms 20 and the assembly of the head and trunk cushions 28 and 26 to the slab 30 permits the entire foam cushion 24 rotated as a single piece by 180° about a vertical axis and replaced on the pallet 12. This permits the orientation of the patient to be in either of two positions along the table so that the patient is received either "head first" or "feet first" within the bore of the MRI magnet as the table of the MRI machine is moved into the bore. Significantly, this can be accomplished without removal of the pallet 12 from the table of the MRI system or the disconnection of cables connecting the coil 10 to the MRI system as will be described below.

Figure 2:
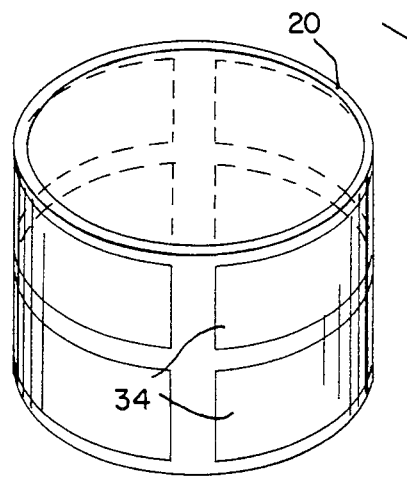
FIG. 2 is an exploded, perspective view of one of the coil forms of FIG. 1 and of the coil which fits within that coil form.
Figure 2:
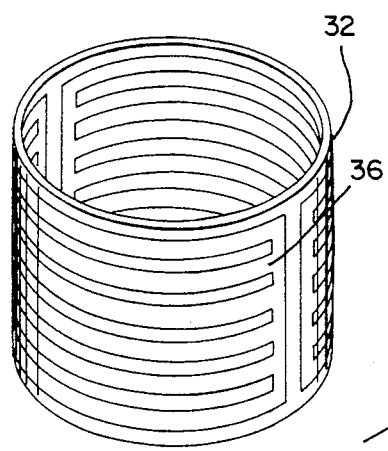

Referring now to FIGS. 1 and 2, the inner surface of each coil form 20 supports a tubular coil 32 and the outer surface of each coil form 20 is surrounded by a tubular shield 34. Each tubular shield 34 is constructed of eight rectangular conductive copper sheets bent to conform to the outer surface of the cylindrical coil form 20. Pairs of sheets are aligned above and below each other on the outer wall of the coil form 20 and each pair is spaced around the form at 90° intervals. The effect is to provide a substantially complete tubular conductor having narrow gaps to prevent large eddy current flows, yet allowing the conduction necessary to provide substantial isolation between the volumes of the coil forms 20, that is, to minimize the inductive path between the volume contained in one coil form 20 and the volume contained in the second coil form 20. Preferably the shields 34 are constructed out of 1 mill copper sheet and spaced from each other by approximately ¼ inch Positioned coaxially within each coil form 20 and shield 34 is a receiving coil 32. Coils 32 are also constructed in the form of a cylindrical tube and are supported by the inner surface of coil form 20. The thinness of the coils 32 provides that the volumes embraced by the coils 32 are substantially equivalent to those of coil forms 20 alone.

Figure 3:
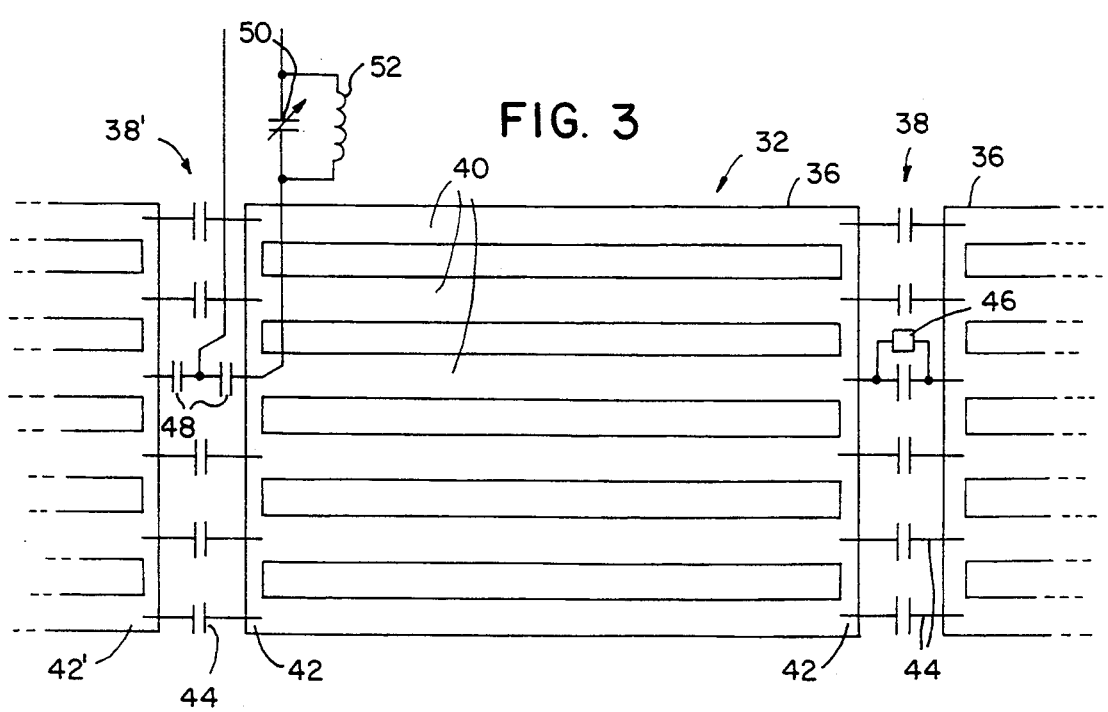
FIG. 3 is a panoramic view of the coil of FIG. 2 showing the formation of multiple conductive loops from two slotted planar conductors connected to each other with capacitors.

Referring to FIGS. 2 and 3, each coil 32 is constructed of two curved, conductive copper sheets 36. The two sheets 36 which oppose each other about the axis of the form 20 and together subtend approximately 360° about that axis. Opposed axially aligned edges of each sheet 36 are spaced from each other by a first and second gap 38 and 38' as will be described below.

Each sheet 36 has a set of six slots extending along lines of circumference of the coil form 20 and which divide the sheet 36 into six circumferential conductors 40 joined by axially oriented end bars 42. Capacitors 44 connect one end of each conductor 40 in each sheet 36 to the corresponding end of the opposing conductor in the other sheet 36. Accordingly, six capacitive elements 44 bridge each gap 38 and 38'.

One centrally located capacitor 44 is shunted by a decoupling circuit network 46 as will be described. A corresponding centrally located capacitor 44 in the other gap 38' is broken into two series connected capacitors 48 to provide a tap to output the NMR signal as will also be described further below. One of the series connected capacitors 48 is shunted by an RF choke 49 which serves to provide a DC path to the decoupling circuit network 46 from coaxial cable 54 to permit active decoupling as will also be described.

It will be understood from the above description that the coil 32 thus consists of a number of separate series resonant loop coils parallel to each other but displaced along the axis of the coil form 20 and connected in parallel at points 180° displaced about their circumference. The inductance of each loop together with its connecting capacitors 44 tunes the loops to resonance at approximately the Larmor frequency of water.

Figure 4:
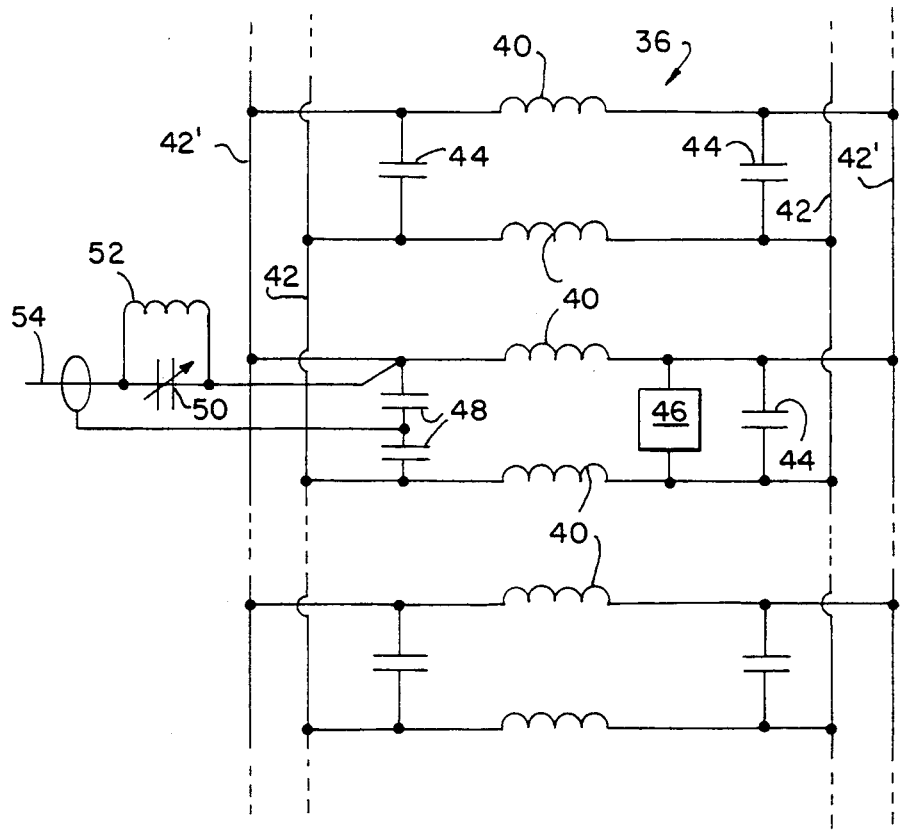
FIG. 4 is a schematic representation of the coil of FIG. 3 as reduced to lumped elements showing the electrical connection used to obtain an electrical signal from the coil structure.

Referring now to FIGS. 3 and 4, the decoupling network 46 connected across a centrally located one of the capacitors 44 is fashioned of a pair of back-to-back diodes in series with an inductance (not shown). The diodes serve to switch the inductance in parallel with its respective capacitor 44 when the voltage across that capacitor 44 is sufficient to bias the diodes into conductance. The inductor is sized so as to create a parallel resonant circuit with the combined capacitance across the gap 38 across which the isolation network 46 connects and thus to block current flow in the coil 32. This effectively decouples the coil 32 from large amplitude radio frequency signals at the Larmor frequency such as are typically present during the excitation of an MRI pulse sequence. The magnitude of the much lower strength RF signal, seen during the detection of the NMR signal from the precessing nuclei, is such as to provide insufficient voltage to bias the diodes into conductance thereby not placing the inductor into parallel resonance during the detection phase. A detailed description of such isolation networks and the selection of components for them is contained in U.S. Pat. No. 5,166,618 assigned to the same assignee as the present invention and hereby incorporated by reference.

As mentioned above, in gap 38', a centrally located capacitor 44 is broken into two series connected capacitors 48 across which the NMR signal may be developed, or into which an exciting RF signal may be injected. The junction of the two capacitors 48 provides a ground reference for the signal and the connection of one capacitor 48 to one of the circumferential conductors 40 provides a signal injection or extraction point. This connection point is connected through a variable capacitor 50 shunted by an inductor 52 to provide an impedance matching network between the coil 32 and a 50 ohm coaxial cable 54 as will be understood in the art. Each of the coils 32 is electrically identical.

The multiple circumferential loops of the coils 32 have been found to provide an even reception pattern within the volume defined by the coil 32 and the coil form 20.

Figure 5:
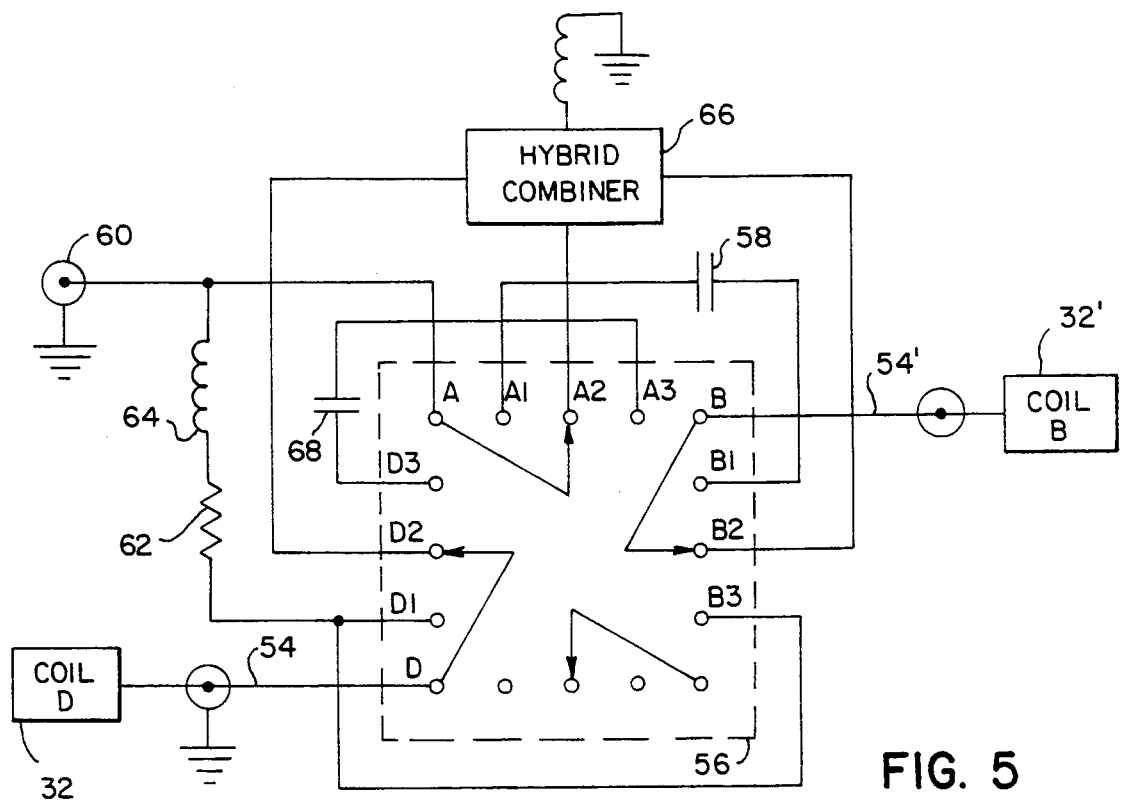
FIG. 5 is a schematic representation of a switch box for connecting the two coils of the two coil forms together for left unilateral, right unilateral, or bi-lateral imaging.

Referring now to FIG. 5, signals from the two coils 32 in the local coil 10 are transmitted along coaxial cables 54 and 54' and a four-pole, triple-throw rotary switch 56. Only three of the four poles are employed, those poles being labeled A, B and D respectively. The corresponding throws are labeled A1, A2, A3 (for pole A), B1, B2, B3 (for pole B) and D1, D2, D3 (for pole D). As the rotary switch 56 is turned, correspondingly numbered throws are connected to their poles at each of the three positions. The three positions provide left unilateral, right unilateral and bilateral imaging as provided in Table I.

TABLE I

| Switch Position | Connected Throws | Function |
| --- | --- | --- |
| 1 | A1, B1, D1 | Left unilateral imaging. Coil D inactivated, Coil B activated. |
| 2 | A2, B2, D2 | Bilateral imaging. Coils D and B activated. |
| 3 | A3, B3, D3 | Right unilateral imaging. Coil B deactivated. Coil D activated. |

In switch position 1, the signal from coil B (32'), passing along coaxial cable 54', is connected through blocking capacitor 58 and is conducted to the coil output 60 which is received by the MRI system (not shown). The blocking capacitor 58 prevents a DC disabling current, provided by the MRI system, from being conducted to coil B and biasing on the diodes of the decoupling circuit network 46 which when so biased would provide active decoupling.

The signal from coil D, passing along coaxial cable 54, is connected through an RF blocking network which is comprised of series connected resistor 62 and inductor 64. This network allows the flow of the DC current from the output 60 into coil D but blocks the radio frequency NMR signal from coil B from being conducted into coil D.

In switch position 2, the signal from coil B, along coaxial 54', is received by one port of hybrid combiner 66. Likewise, the signal from coil D along coaxial cable 54 is received by a second port of the hybrid combiner 66 which adds the signals together, without phase shift, and provides the sum at a third output which is connected to the coil output 60. The hybrid combiner is a Wilkinson hybrid combiner such as is known in the art which provides an implicit DC current blocking to prevent the DC current from the output 60 from deactivating coils B and D through their isolation networks 46. Hybrid networks are four port networks known in the art and having the property that when the four ports are properly terminated, energy input to two of the ports, if the proper relative phase angles (in this case 0°) will be combined at one of the remaining ports. Likewise, the signal appearing at one of the ports will be split into two signals of the proper phase angle which will appear at the unterminated outputs of the other two ports. The third port of the hybrid combiner is typically terminated in a manner to preserve the proper impedance relationships as is understood in the art. A hybrid network also provides a degree of isolation between the two ports that receive the NMR signals.

In switch position 3, the signal from coil D, along coaxial cable 54, is communicated through blocking capacitor 68 to the output of the coil 60 while the signal from coil B, along coaxial cable 54', is connected to the network consisting of resistor 62 and inductor 64 which allows the conduction of DC current from the output 60 to the coil B, disabling coil B by means of its decoupling circuit network 46.

Thus, the signal produced at the output of the coil 60, depending on the position of the switch 56, may be the signal from either breast or a combined signal from both breasts as may be desired.

Figure 6:
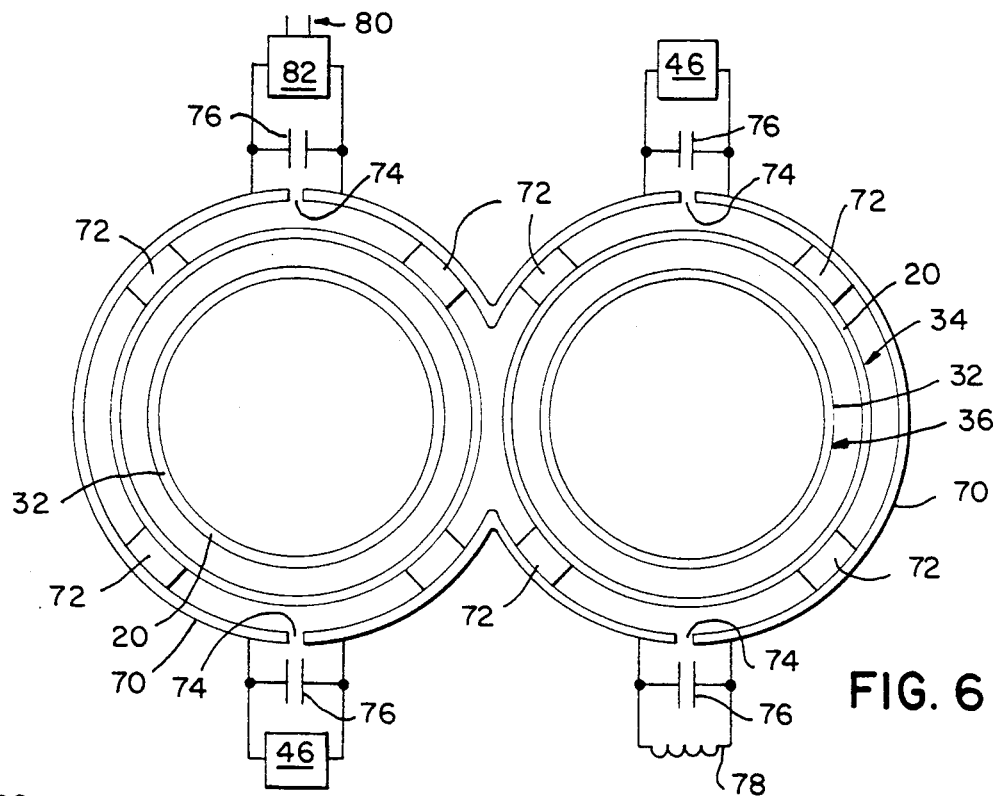
FIG. 6 is a plan view of a second embodiment of the coil forms incorporating a figure-eight coil for the use in imaging both breasts.
Figure 7:
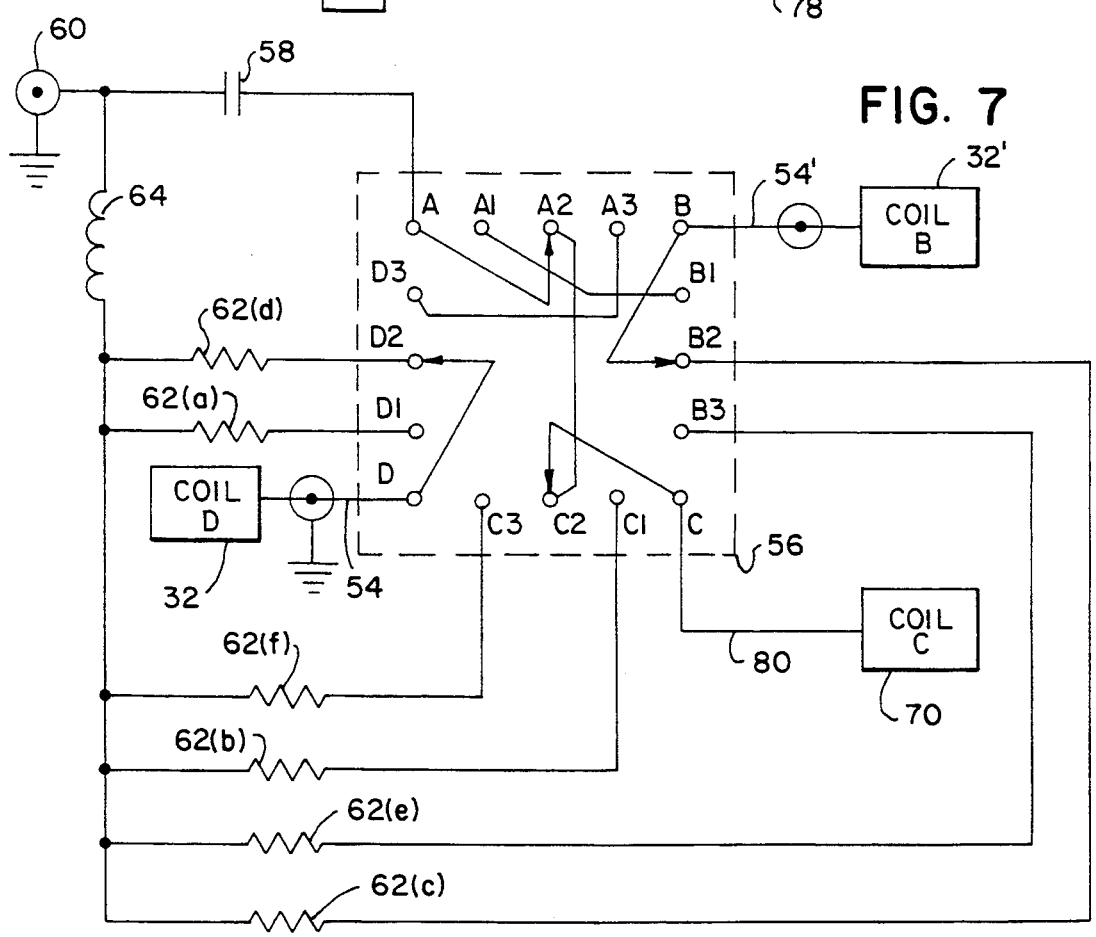
FIG. 7 is a schematic representation of a switch box for connecting the three coils of the two coil forms and the figure-eight coil together for either left unilateral, right unilateral, or bilateral imaging.

Referring to FIGS. 6 and 7, improved bilateral reception of the NMR signal is obtained by the use of a third coil 70 being a single loop fitting about the shield tubes 34 in the form of a figure-eight. The coil 70 conforms generally to the outer surface of the shield tubes 34 and is positioned towards the upper supporting surface of the cowling 22 by means of insulating support clips 72. The coil 70 is preferentially constructed of copper tubing bent into the desired figure-eight form.

Coil 70 is broken by gaps 74 spaced at approximately equal intervals around the loop of coil 70 across which resonating capacitors 76 are placed so as to tune coil 70 to the same resonance as coils 32. Placed symmetrically on the coil 70, across two of the gaps 74 are decoupling networks 76, as have been previously described, for decoupling the coil 70 from the RF field during the excitation stage of the MRI pulse sequence or when actively disabled as will be described. One of the remaining gaps 74 and its resonating capacitor 76 is shunted by an inductor 78 to provide passage for an active decoupling DC current through both of the isolation networks 76. This DC current may be received by a coaxial cable 80 connected to the coil 70 by means of a matching network 82 shunting the remaining gap 74. Thus, the coil 70 forms a single loop about both breasts when they are positioned within the coil forms 20 to provide for bilateral imaging.

The three coil embodiment of FIG. 6 requires a different configuration of the switch box 56 as is shown in FIG. 7. In this embodiment, the three positions of switch 56 as previously described, as before, provide left unilateral, right unilateral and bilateral imaging as indicated in Table II.

TABLE II

| Switch Position | Connected Throws | Function |
| --- | --- | --- |
| 1 | A1, B1, C1, D1 | Left unilateral imaging. Coils D and C inactivated, Coil B activated. |
| 2 | A2, B2, C2, D2 | Bilateral imaging. Coils D and B deactivated, Coil C activated. |
| 3 | A3, B3, C3, D3 | Right unilateral imaging. Coil B and C deactivated. Coil D activated. |

In switch position 1, the signal from coil B (32'), passing along coaxial cable 54' is connected through blocking capacitor 58 to the coil output 60 as received by the MRI system (not shown). Again, the blocking capacitor 58 prevents a DC disabling current, provided by the MRI system, from being conducted to coil B and biasing on the diodes of the decoupling circuit network 56 which when so biased would provide active decoupling.

A signal from coil D, passing along coaxial cable 54, is connected through an RF blocking network which is comprised of a series connected resistor 62(a) and inductor 64. Likewise, coil C is connected by coaxial cable 80 to an RF blocking network comprised of series connected resistor 62 (b) and inductor 64. These networks allow the flow of DC current from the output 60 to coils D and C but block the radio frequency NMR signal from coil B from being conducted into coil D.

In switch position 2, the signal from coil C along coaxial cable 80, is connected to the blocking capacitor 58 and conducted to the coil output 60 to be received by the MRI system. Correspondingly, coils B and D receive the DC current from the output 60: in the former case through series connected conductor 64 and resistor 62(c), and in the latter case through series connected inductor 64 and resistor 62(d).

Finally, in switch position 3, the signal from coil D, along coaxial cable 54 is communicated through blocking capacitor 58 to the output of the coil 60 while the signals from coils B and C are connected to the DC current from the MRI system received at output 60 through, in the former case, series connected inductor 64 and resistor 62(e) and in the latter case, through series connected inductor 64 and resistor 62(f).

Thus, the signal produced at the output of coil 60, depending on the position of switch 56, may be the signal from either breast or the combined signals from both breasts as received by third coil 70.

The above description has been that of a preferred embodiment of the present invention which will occur to those who practice the art that many modifications may be made without departing from the spirit and scope of the invention. For example, as mentioned, the coil may be used as both receive and transmit coil with relatively minor modifications as noted. In order to apprise the public of the various embodiments that may fall within the scope of the invention, the following claims are made.

We claim:

1. An MRI radio frequency coil suitable for imaging a first and second human breast comprising:
    a first and second coil form defining adjacent volumes disposed and sized for receiving, respectively, the first and second breast through open first ends of the first and second coil forms;
    a first and second coil attached to the first and second coil forms, respectively, so as to receive a first and second RF signal from the volumes of the first and second coil forms, respectively,
    a radio frequency shield positioned between the first and second coil to limit the sensitivity of the first coil to the second RF signal in the second volume and to limit the sensitivity of the second coil to the first RF signal in the first volume and;
    a third coil surrounding the first and second coil forms so as to receive the combined first and second RF signal from the volumes of the first and second coil forms, respectively.

2. An MRI radio frequency coil suitable for imaging a first and second human breast comprising:
    a first and second coil form defining adjacent volumes disposed and sized for receiving, respectively, the first and second breast through open first ends of the first and second coil forms;
    a first and second coil attached to the first and second coil forms, respectively, so as to receive a first and second RF signal from the volumes of the first and second coil forms, respectively, and
    a radio frequency shield positioned between the first and second coil to limit the sensitivity of the first coil to the second RF signal in the second volume and to limit the sensitivity of the second coil to the first RF signal in the first volume including in addition:
    a first and second decoupling network attached to the first and second coil, respectively, to de-tune the first and second coil upon receipt of a decoupling signal;
    a switchbox receiving a first and second electrical current from the first and second coils, the first and second currents being proportional to the first and second RF signals, the switch box having:
        a first position wherein the first electrical current is conducted to a switchbox output and a DC decoupling signal is conducted to the second coil;
        a second position wherein the second electrical current is conducted to the switch box output and a DC decoupling signal is conducted to the first coil; and
        a third position wherein the first electrical current is summed in a combiner network to the second electrical current and conducted to the switchbox output.

3. An MRI radio frequency coil suitable for imaging a first and second human breast of a patient in an MRI machine having a supporting table, the coil comprising:
    a pallet adopted to fit against an upper surface of the table to be held by the same;
    a first and second coil form defining adjacent volumes disposed and sized for receiving, respectively, the first and second breast through open first ends of the first and second coil forms, and attached to an upper surface of the pallet at second ends opposed to the first ends and extending upward from the upper surface by a height;
    a first and second coil attached to the first and second coil forms, respectively, so as to receive a first and second RF signal from the volumes of the first and second coil forms, respectively;
    a removable cushion having:
    a first portion fitting against the upper surface of the pallet and extending the height above the upper surface against a first side of the first and second coil form to support head and shoulders of the patient when the patient is positioned on the coil forms; and
    a second portion fitting against the upper surface of the pallet and extending the height above the upper surface against a second side of the first and second coil form to support the trunk of the patient when the patient is positioned on the coil forms;
    wherein the first and second portions of the removal cushion may be interchanged to accommodate head first or feet first positioning of the patient on the table without movement of the pallet.

* * * * *